United States Patent [19]

Schaeffer et al.

[11] Patent Number: 5,188,802

[45] Date of Patent: Feb. 23, 1993

[54] DRY ANALYTICAL ELEMENT FOR LITHIUM ASSAY

[75] Inventors: James R. Schaeffer, Penfield; Ronald H. Engebrecht, Victor; Robert F. Winterkorn, Rochester; Harold C. Warren, III, Rush; Thomas R. Welter, Webster, all of N.Y.

[73] Assignee: Eastman Kodak Company, Rochester, N.Y.

[21] Appl. No.: 706,434

[22] Filed: May 28, 1991

[51] Int. Cl.$^5$ ...................... G01N 21/00; G01N 33/20
[52] U.S. Cl. ........................................ 422/56; 422/57; 436/79
[58] Field of Search ............... 436/79, 74, 70; 422/55, 422/50, 56, 57, 58

[56] References Cited

U.S. PATENT DOCUMENTS 4,859,606  8/1989  Cram et al. ........................... 422/50

FOREIGN PATENT DOCUMENTS 62-72683  4/1987  Japan .

OTHER PUBLICATIONS

Kimura et al, J. Org. Chem., vol. 52 (1987), 836–844.

Primary Examiner—James C. Housel
Assistant Examiner—Lyle A. Alexander
Attorney, Agent, or Firm—John R. Everett

[57] ABSTRACT

A novel 14-crown 4-ether derivative is disclosed for use in a dry analytical element for assaying lithium.

6 Claims, No Drawings

DRY ANALYTICAL ELEMENT FOR LITHIUM ASSAY

FIELD OF THE INVENTION

This invention relates to the field of clinical chemistry, particularly elements for assaying lithium in serum.

BACKGROUND

Lithium in the form of lithium carbonate is administered to manic-depressive patients. The therapeutic range of lithium ion in plasma is quite narrow, namely, 0.8 to 1.2 mM. It is important to monitor the lithium level in such patients because of the toxic side effects that appear when the lithium level in blood exceeds the recommended level.

It is known to assay lithium quantitatively using solution assays and ion-selective electrodes. Dyes, such as 14-Crown-4-ether derivatives are known for use in such assays. Japanese Kokai 62/72683 (1985) discloses a class of such dyes that act as colorometric reagents in extracting lithium from solutions and as charge transport carriers for ion-selective electrodes. The problem is that none of the known 14-crown-4-ether derivatives can be adapted for use in dry analytical elements. Moreover the above "wet" methods involving solution extractions or ion-selective electrodes suffer from severe ion and other interferant problems. It would be desirable to have a dry analytical element for assaying lithium that obviated these problems.

SUMMARY OF THE INVENTION

This invention provides a multilayer dry analytical element for quantitatively assaying lithium comprising a spreading layer, and a reagent layer characterized in that sufficient buffer is present in a layer above the reagent layer to establish a pH of at least 9 and the reagent layer comprises a 14-Crown-4-ether derivative selected from Table 1 below:

TABLE 1

14-Crown-4-Ether Derivatives

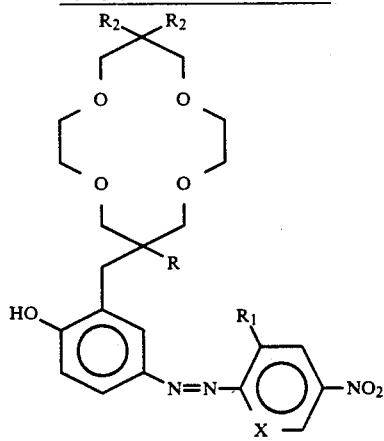

| Dye No. | R | $R_1$ | $R_2$ | X |
|---|---|---|---|---|
| 1 | n-$C_{12}H_{25}$ | $SO_2CH_3$ | $CH_3$ | CH |
| 2 | n-$C_{12}H_{25}$ | $NO_2$ | $CH_3$ | CH |
| 3 | $CH_3$ | $SO_2N(n-C_6H_{13})_2$ | $CH_3$ | CH |
| 4 | $CH_2C_6H_5$ | $SO_2N(n-C_6H_{13})_2$ | $CH_3$ | CH |
| 5 | $CH_2C_6H_5$ | $SO_2N(CH_3)-n-C_{18}H_{37}$ | $CH_3$ | CH |
| 6 | $CH_3$ | $NO_2$ | n-$C_7H_{15}$ | CH |
| 7 | n-$C_{12}H_{25}$ | H | $CH_3$ | N |

Using the element of this invention a colorometric assay for lithium can be performed directly on the sample without deproteinization. The use of the above selected dyes of Table 1 is unobvious, since not all 14-Crown-4-ether derivatives are useful even in solution assays of lithium.

DETAILED DESCRIPTION OF THE INVENTION

The following procedures was used to prepare dyes 2-8, 11-13 of Table 2, infra. The procedure comprises the steps of:

a) reducing a 2-substituted-2-[2,5-bis(alkoxy)benzyl]-malonate ester with a strong reducing agent to produce a 2-substituted-2-[2,5-bis(alkoxy)benzyl]-1,3-propanediol, said alkoxy group being benzyloxy or unsubstituted alkoxy of 1 to 10 carbon atoms, b) condensing the 1,3-propanediol of step a) with a 5,5-disubstituted-3,7-dioxanonane-1,9-diylbis(toluene p-sulfonate) to form a 6,13,13-trisubstituted-6-[2,5-bis-(alkoxy)benzyl]-1,4,8,11-tetraoxacyclotetradecane, c) hydrogenating the bis(alkoxy) compound of step b) to the hydroquinone, 6,13,13-trisubstituted-6-(2,5-dihydroxybenzyl)-1,4,8,11-tetraoxacyclotetradecane, d) oxidizing the hydroquinone of step c) to the quinone, 6,13,13-trisubstituted-6-(1,4-cyclohexadiene-3,6-dione-1-ylmethyl)-1,4,8,11-tetraoxacyclotetradecane, and e) condensing the quinone of step d) with an N-(p-nitrophenyl)hydrazine to produce the 14-crown-4-ether azo dye product.

Preparation Sequence I

The preparation of the diol portion of the dyes is shown in Sequence I, infra. A 2,5-dibenzyloxybenzyl chloride, compound 1, is condensed with dimethyl 2-alkylmalonate, compound 2, yielding a 2-substituted-2-[2,5-bis(alkoxy)benzyl]malonate ester, compound 3, which is subsequently reduced with a strong reducing agent to produce a 2-substituted-2-[2,5-bis(alkoxy)benzyl]-1,3-propanediol, said alkoxy group being benzyloxy or unsubstituted alkoxy of 1 to 10 carbon atoms, compound 4.

SEQUENCE I

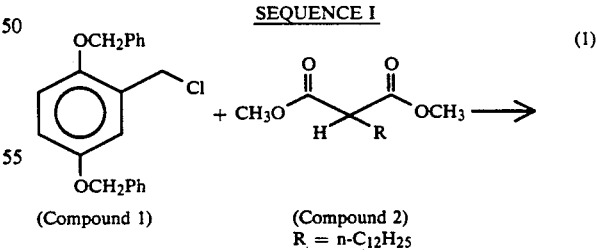

(Compound 1)

(Compound 2)
R = n-$C_{12}H_{25}$

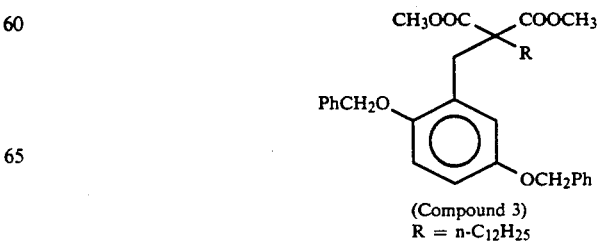

(Compound 3)
R = n-$C_{12}H_{25}$

-continued
SEQUENCE I

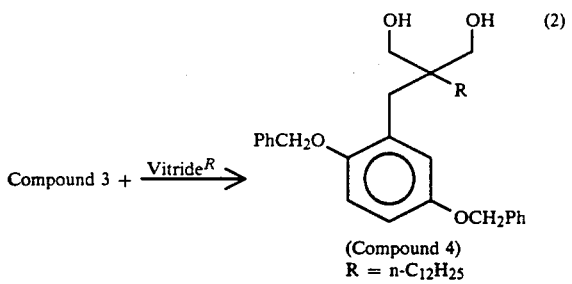

(Compound 4)
R = n-C$_{12}$H$_{25}$

1. Preparation of dimethyl 2-dodecyl-2-[2,5-bis(benzyloxy)benzyl]malonate (Compound 3)

A solution of 121.4 g (404.7 mol) of Compound 2 (dimethyl 2-dodecylmalonate) in 600 mL of dimethylformamide was added to 56.0 g (500 mmol) of potassium tert. butoxide. After 30 minutes the reaction mixture was cooled to 0° C. and 137 g (404.7 mmol) of Compound 1, 2-(chloromethyl)-1,4-bis(phenylmethoxy)benzene, was added and the mixture allowed to warm to room temperature for 30 minutes. The mixture was next heated at 60° C. for 90 minutes and an additional 4.5 g of Compound 2 and 4.5 g of potassium tertiary butoxide was added. The reaction mixture was then heated at 60° C. for 10 hours. Removal of the solvent yielded a viscous oil. This oil was partitioned between ethyl acetate and dilute hydrochloric acid, and the organic phase dried over anhydrous sodium sulfate, filtered and concentrated to yield an impure viscous oil (Compound 3). Compound 3 was used as prepared in the next step.

2. Preparation of 2-dodecyl-2-(2,5-di(benzyloxy)benzyl)-1,3-propanediol (Compound 4)

A solution of 302.4 g (502.3 mmol) of Compound 3 in 2 L of toluene was prepared. Then 200 mL of the toluene was distilled off to remove residual water. After cooling to room temperature 303.2 g (1.05 mol) of sodium bis(2-methoxyethoxy)aluminum hydride (Vitride ®) was added and the solution stirred for four hours. The reaction was quenched with 90 mL of water, 90 mL 15% sodium hydroxide and 275 mL water. The toluene phase was isolated and the aqueous phase extracted with 500 mL of toluene. The combined organic extracts were dried over anhydrous sodium sulfate, filtered and the solvent removed. The resulting oily product was triturated with petroleum ether. The resulting solid was filtered and washed with petroleum ether yielding a compound having an $^1$H NMR spectrum consistent with the structure of compound 4 (melting point 64°-65° C.).

The final preparation steps for making the proton-ionizable 14-crown-4-ether dyes (Dyes 2-7 and 10-12 of Table 2) are shown in Sequence II. The initial ionophore is formed by condensation of 1,3-propanediol, compound 4, with a 5,5-disubstituted-3,7-dioxanonane-1,9-diylbis(toluene p-sulfonate), compound 9, a ditosylate, to form a 6,13,13-trisubstituted-6-[2,5-bis(alkoxy)-benzyl]-1,4,8,11-tetraoxa-cyclotetradecane, Compound 5. Compound 9 was prepared according to methods described in the literature. Compound 5 is then hydrogenated to the hydroquinone, 6,13,13-trisubstituted-6-(2,5-dihydroxybenzyl)-1,4,8,11-tetraoxacyclotetradecane, compound 6. Compound 6 is then oxidized to yield 6,13,13-trisubstituted-6-(1,4-cyclohexadiene-3,6-dione-1-ylmethyl)-1,4,8,11-tetraoxacyclotetradecane, Compound 7. The desired dyes are then prepared by condensation of the quinone, Compound 7, with an N-(p-nitrophenyl)hydrazine to produce the 14-crown-4-ether azo dye product, Compound 8.

SEQUENCE II

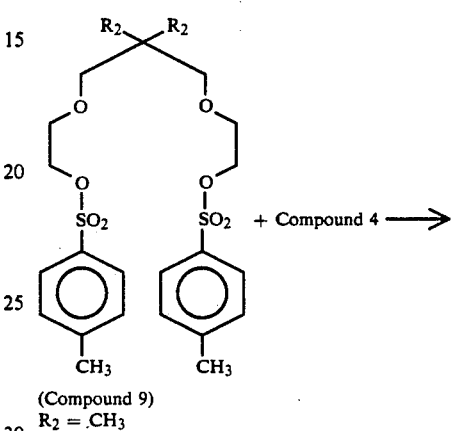

(Compound 9)
R$_2$ = CH$_3$

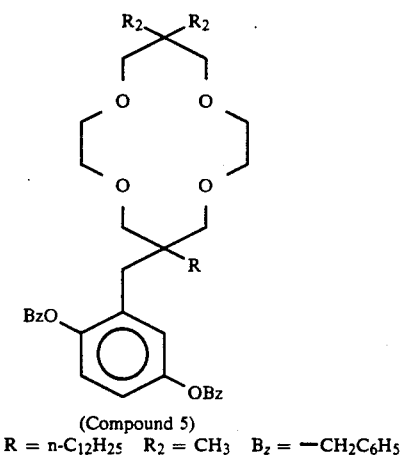

(Compound 5)
R = n-C$_{12}$H$_{25}$   R$_2$ = CH$_3$   B$_z$ = —CH$_2$C$_6$H$_5$

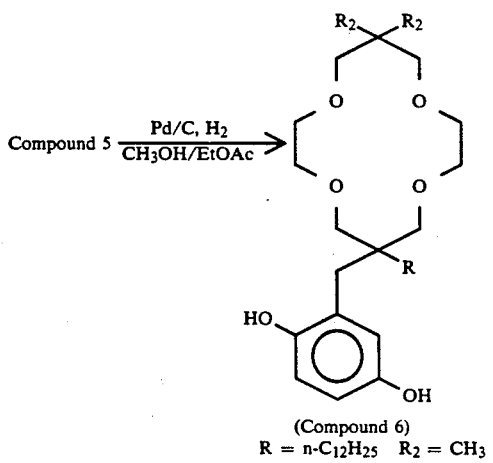

(Compound 6)
R = n-C$_{12}$H$_{25}$   R$_2$ = CH$_3$

-continued
SEQUENCE II

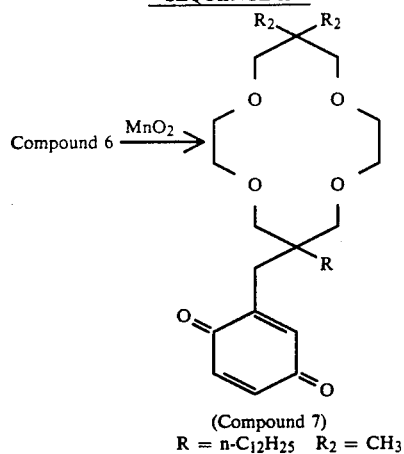

(Compound 7)
R = n-C$_{12}$H$_{25}$  R$_2$ = CH$_3$

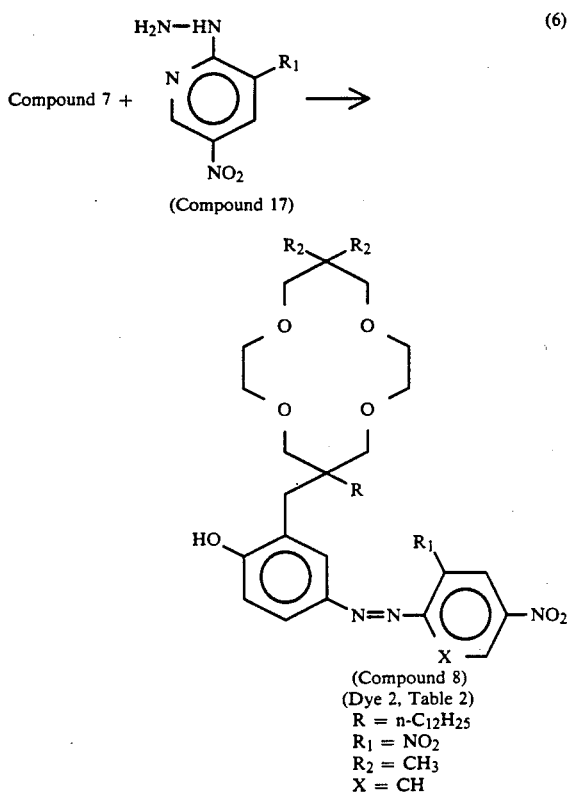

(Compound 8)
(Dye 2, Table 2)
R = n-C$_{12}$H$_{25}$
R$_1$ = NO$_2$
R$_2$ = CH$_3$
X = CH 3. Preparation of 6-Dodecyl-6-[2,5-di(benzyloxy)benzyl]-13,13-dimethyl-1,4,8,11-tetraoxacyclotetradecane (Compound 5)

A suspension of 110 g (219.8 mmol) of compound 9, 5,5-dimethyl-3,7-dioxanonane-1,9-diylbis(toluene p-sulfonate), 120 g (219.8 mmol) of compound 4 and 12.2 g (220 mmol) of lithium bromide in 2 L of dry t-pentyl alcohol was reacted with 7.0 g of lithium hydride. After refluxing the reaction mixture for 7 days the solvent was removed and the residue dissolved in a mixture of dichloromethane and dilute hydrochloric acid. The dichloromethane phase was separated, dried over anhydrous magnesium sulfate, filtered and concentrated to a dark oil. The oil was dissolved in 10% dichloromethane 90% petroleum ether and eluted through a silica gel column (600 g) the fractions containing the product (silica gel TLC/CH$_2$Cl$_2$, Rf 0.2) were combined to yield 83.2 g of impure product (Compound 5).

4. Preparation of 6-Dodecyl-6-(2,5-dihydroxybenzyl)-13,13-dimethyl-1,4,8,11-tetraoxacyclotetradecane (Compound 6)

A solution of 15.8 g (22.5 mmol) of Compound 5 in 20 mL of ethyl acetate and 20 mL of methanol was mixed with 0.4 g of palladium-on-carbon in a parr flask under a nitrogen atmosphere. The mixture was reacted at 50°-60° C. under 50 psi H$_2$ for 4 hours. After cooling, the product was filtered through Celite diatomaceous earth and the solvent removed to yield 12.7 g of impure product (Compound 6).

5. Preparation of 6-Dodecyl-6-(1,4-cyclohexadiene-3,6-dione-1-ylmethyl)-13,13-dimethyl-1,4,8,11-tetraoxacyclotetradecane (Compound 7)

A solution of 67.6 g (129.3 mmol) of Compound 6 in 600 mL of dichloromethane was mixed with 50.6 g (581.9 mmol) of activated manganese dioxide. The heterogeneous mixture was stirred at room temperature for 1 hour. The insolubles were removed by filtration through Celite diatomaceous earth and the solvent removed. The oily residue was triturated with 500 mL of petroleum ether and cooled. The volume of solvent was reduced to ½ and the yellow solid suction filtered and washed with cold pentane.

A first and second fraction of compound 7 was isolated, giving a $^1$H NMR spectrum consistent with the assigned structure.

6. Preparation of 6-dodecyl-6-[2-hydroxy-5-(2,4-dinitrophenylazo)benzyl]-13,13-dimethyl-1,4,8,11-tetraoxacyclotetradecane [Compound 8 (dye 2, Table 2)]

A solution of 31.7 g (60.9 mmol) of compound 7 and 14.2 g (60.9 mmol) of 2,4-dinitrophenylhydrazine (15% H2O) in 300 cc of acetic acid was heated at 60° C. for 90 minute with constant stirring. After removing 225 mL of acetic acid, the product was added to 500 mL of petroleum ether. Initially several g of product was recovered. After recrystallization from dichloromethane/petroleun ether compound 8 was obtained, mp 64°-65° C. The $^1$H NMR spectrum was consistent with the assigned structure.

Preparation Sequence III

An alternative method was used to prepare Dyes 1, and 8–9 of Table 2. This method is illustrated in Sequence III. The diol used in the sequence was prepared by the condensation of o-benzyloxybenzl chloride, compound 10, with dialky 2-dodecyl- or 2-methyl- or 2-phenylmalonate, to form a substituted diakyl malonate, compounds 2 or 11b–c. The substituted dialkyl malonate (compounds 12a–c, were subsequently reduced to the diol (compounds 13a–c).

The reaction of the ditosylate, compound 9, and diols compound 13a, b, c) yield the corresponding 14-crown-4 ionophore compounds 14a, b and c. Subsequent hydrogenation yields the proton-ionizable 14-crown-4-ether compounds 15a, b and c which are then converted into dyes by coupling with a diazonium salt.

SEQUENCE III

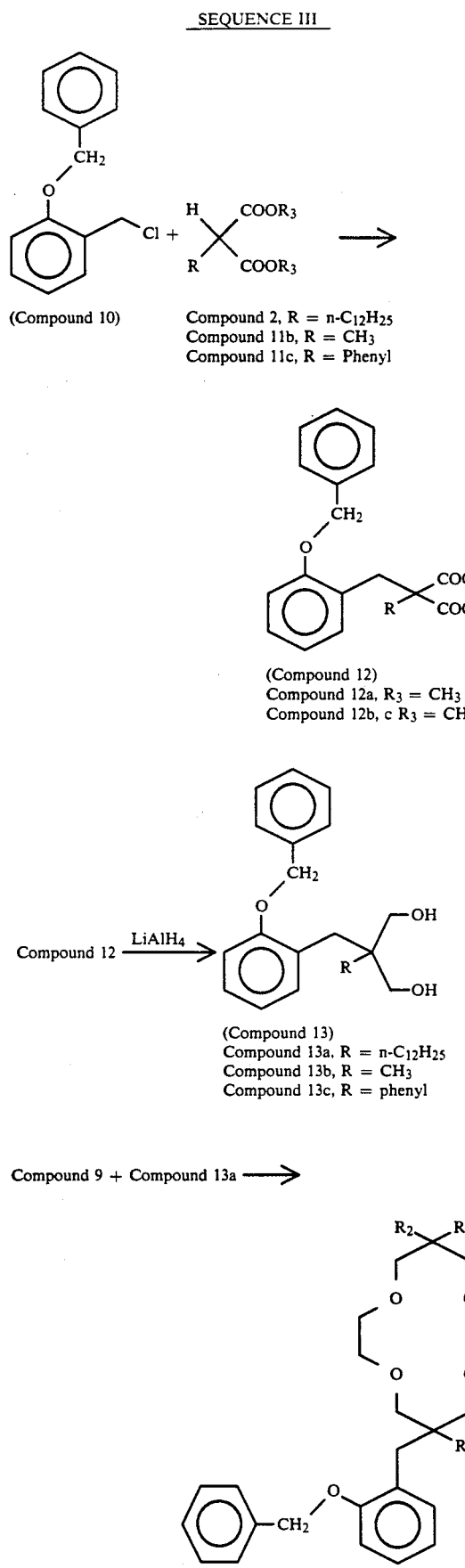

(Compound 10)

Compound 2, R = n-C₁₂H₂₅
Compound 11b, R = CH₃
Compound 11c, R = Phenyl (Compound 12)
Compound 12a, R₃ = CH₃
Compound 12b, c R₃ = CH₂CH₃

Compound 12 $\xrightarrow{\text{LiAlH}_4}$ (Compound 13)
Compound 13a, R = n-C₁₂H₂₅
Compound 13b, R = CH₃
Compound 13c, R = phenyl Compound 9 + Compound 13a ⟶

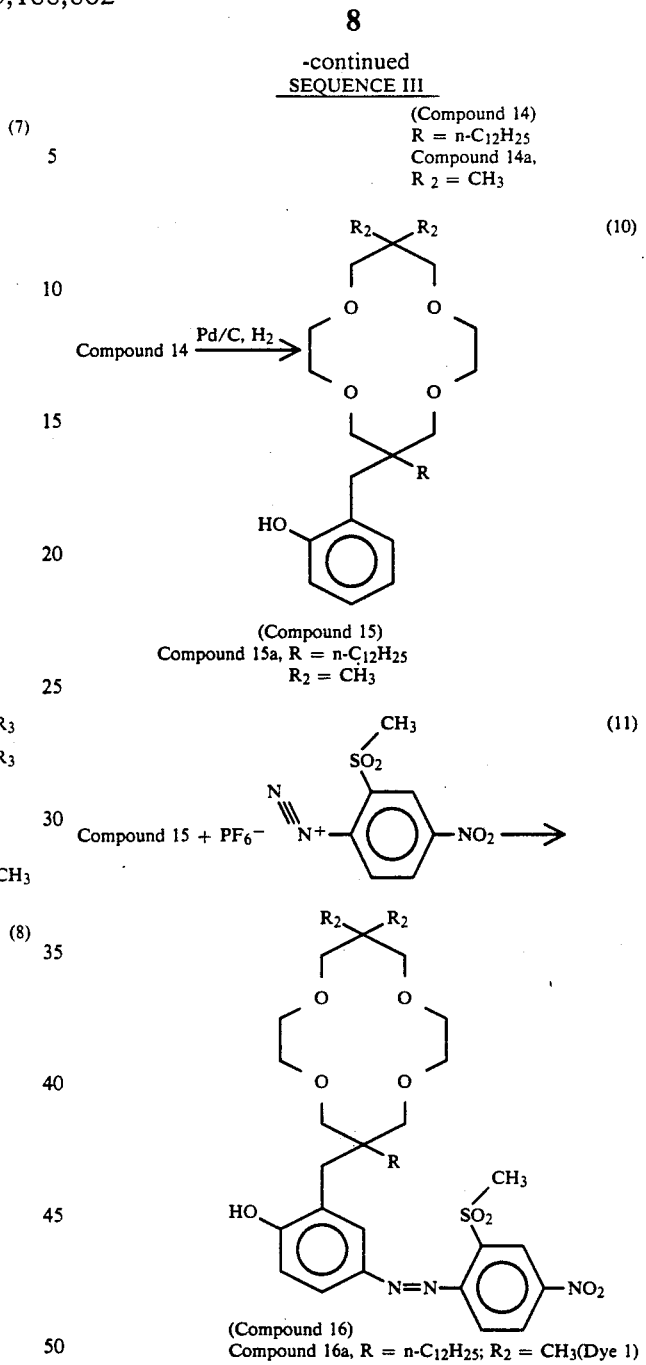

-continued
SEQUENCE III (Compound 14)
R = n-C₁₂H₂₅
Compound 14a,
R₂ = CH₃

Compound 14 $\xrightarrow{\text{Pd/C, H}_2}$ (Compound 15)
Compound 15a, R = n-C₁₂H₂₅
R₂ = CH₃

Compound 15 + PF₆⁻

(Compound 16)
Compound 16a, R = n-C₁₂H₂₅; R₂ = CH₃(Dye 1)

7. Preparation of dimethyl 2-dodecyl-2-(2-benzyloxybenzyl)malonate (Compound 12a)

A solution of 162.6 g (541.3 mmol) of dimethyl 2-dodecylmalonate (Compound 2) in 800 mL of dimethylformamide was mixed with 67.2 g (600 mmol of potassium tertiary butoxide under a nitrogen atmosphere. After cooling to room temperature 116.0 g (541.3 mmol) of 2-(benzyloxy)benzyl chloride was added and the mixture heated at 75° C. for 2 hr. The product was poured over ice/water, extracted twice with ethyl acetate, dried, filtered and isolated as an oily product. This was used as recovered in the next step. The methyl and phenyl derivatives were prepared in a similar manner (See Sequence III).

8. Preparation of 2-dodecyl-2-(2-benzyloxybenzyl)-1,3-propanediol (Compound 13a)

A solution of 260 g (524 mmoles) of compound 12a in 1 L of tetrahydrofuran (THF) was added to a suspension of 29.9 g (786 mmol) of lithium aluminum hydride in 500 mL of dry THF. The reaction mixture was refluxed for 2 hours and then quenched successively with isopropanol and dilute hydrochloric acid. The product was extracted into ether, dried, filtered and concentrated to dryness.

9. Preparation of 6-dodecyl-6-(2-benzyloxybenzyl)-13,13-dimethyl-1,4,8,11-tetraoxacyclotetradecane (Compound 14a)

A solution of 40 g (80 mmol) of Compound 9 and 35.2 g (80 mmol) of Compound 13a in 400 mL of dry dimethylformamide (DMF) was slowly added to a suspension of 13.4 g (560 mmol) of sodium hydride and 21.4 g (160 mmol) of lithium iodide in 200 mL of DMF at 70° C. The reaction product was heated for 24 hours, cooled and the solvent removed. The $^1$H nmr spectrum of the product is consistent with the assigned structure. The product was extracted into ethyl acetate and washed with dilute hydrochloric acid, then twice with a saturated salt solution, dried over anhydrous magnesium sulfate, filtered and the solvent removed. The product was eluted through a silica gel column, yielding 13.8 g (28.9%). The $^1$H NMR spectrum of Compound 14a is consistent with the assigned structure.

10. Preparation of 6-dodecyl-6-(2-hydroxybenzyl)-13,13-dimethyl-1,4,8,11-tetraoxacyclotetradecane (Compound 15)

A solution of 13.3 g (22.3 mmol) of compound 14 in 200 cc of tetrahydrofuran and 150 cc of acetic acid was mixed with 8.0 g of Pd on carbon. The suspension was hydrogenated at 55 psi for 16 hours at room temperature. After filtration and removal of the solvent Compound 15 was isolated. The $^1$H nmr spectrum is consistent with the assigned structure.

11. Preparation of 6-Dodecyl-6-[2-hydroxy-5-(2-methylsulfonyl-4-nitrophenylazo)benzyl]-13,13-dimethyl-1,4,8,11-tetraoxaacyclotetradecane (Compound 16)

To a solution of 3.1 g (6.1 mmol) of Compound 15 in 50 cc acetic acid at 5° C. was added a solution of 3.0 g (8.0 mmol) of 2-methylsulfonyl-4-nitrophenyldiazonium hexafluorophosphate in 25 cc water and 75 cc tetrahydrofuran. The suspension was stirred at room temperature for 16 hours. The product was extracted into ethyl acetate and isolated by silica gel chromatography yielding 0.22 g (4.7%) of Compound 16. The $^1$H nmr spectrum is consistent with the assigned structure.

The following screening procedure was used to identify those 14-Crown-4 ether derivatives that would be useful in formulating a dry analytical element for quantitatively assaying lithium. The data show that some, but not all, derivatives are useful for conducting lithium assays.

Three mL of a 10% dimethyl sulfoxide-water solution containing $3.42 \times 10^{-5}$ mole of a 14-crown-4-ether dye, 50 μL of a 1M pH 11 buffer (4-Aminobutyric acid [CAPS]) and 50 μL of aqueous lithium chloride solution was mixed in a disposable cuvette. Lithium solutions were added at the levels 0.0195, 0.0975 and 0.1952 mM which produced mixtures containing 0.32, 1.61 and 3.2 mM lithium respectively. Absorbance was measured immediately at $\gamma = 600$ nm and again after 5 minutes to monitor the progress of lithium complexing by the 14-crown-4-ether dye. The spectrum of each solution was measured between 300 and 800 nm after each 600 nm absorbance measurement. This measurement allows monitoring of the 14-crown-4-ether absorbance maximum decrease at 400 nm as the lithium is complexed with the dye and a concurrent increase in the absorbance maximum at 600 nm. The delta absorbance values for a representative number of the dyes tested between 0.32 and 3.2 nm are listed in Table 2. Crown ether dyelithium complexes possessing delta absorbance values $\geq 0.12$ are considered satisfactory for use in a dry analytical element for lithium assay provided by the present invention.

TABLE 2

DELTA $D_T$ OF 14-CROWN-4 ETHER DERIVATIVES

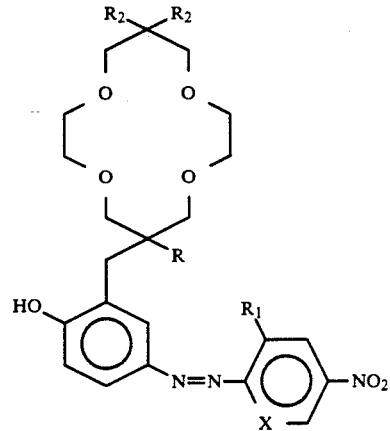

| Dye No. | R | $R_1$ | $R_2$ | X | Delta $D_T$ 3.2–.32 nM |
|---|---|---|---|---|---|
| 1 | n-$C_{12}H_{25}$ | $SO_2CH_3$ | $CH_3$ | CH | 0.57 |
| 2 | n-$C_{12}H_{25}$ | $NO_2$ | $CH_3$ | CH | 0.46 |
| 3 | $CH_3$ | $SO_2N(n-C_6H_{13})_2$ | $CH_3$ | CH | 0.31 |
| 4 | $CH_2C_6H_5$ | $SO_2N(n-C_6H_{13})_2$ | $CH_3$ | CH | 0.12 |
| 5 | $CH_2C_6H_5$ | $SO_2N(CH_3)$-n-$C_{18}H_{37}$) | $CH_3$ | CH | 0.18 |
| 6 | $CH_3$ | $NO_2$ | n-$C_7H_{15}$ | CH | 0.22 |
| 7 | n-$C_{12}H_{25}$ | H | $CH_3$ | N | 0.22 |
| 8 | $CH_3$ | $SO_2CH_3$ | $CH_3$ | CH | <0.1 |
| 9 | $C_6H_5$ | $SO_2CH_3$ | $CH_3$ | CH | <0.1 |
| 10 | $C_6H_5$ | $NO_2$ | $CH_3$ | CH | <0.1 |
| 11 | $CH_2C_6H_5$ | $NO_2$ | $CH_3$ | CH | <0.1 |
| 12 | n-$C_{12}H_{25}$ | H | $CH_3$ | CH | 0.09 |

Phosphate Buffer pH 11.7

The data of Table 2 show that, of the dyes presented, only dyes 1–7 meet $D_T$ criteria for use in a dry analytical element.

The element of this invention can be used to assay lithium qualitatively and quantitatively in biological fluids in animals or humans, but preferably in humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Elements of the invention can be configured in a variety of forms, including elongated tapes of any desired width, sheets, slides or chips.

The elements can be used in manual or automated assay techniques. In general, in using the elements, lithium determination is made by taking the element from a supply roll, chip packet or other source and physically contacting it with a sample (for example, up to 200 μL) of the liquid to be tested so that the sample and reagents interact sequentially within the element and become mixed. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation, we simply mean that the reagents are maintained in contact with each other for a period of up to 5 minutes before color measurements are made.

The dry analytical elements of this invention are multilayered. In one embodiment the element includes a spreading layer, a subbing layer which contains buffer and an additional reagent layer having at least two distinct zones. All of the foregoing layers are coated on a support.

Another embodiment includes a combined reagent/spreading layer along with a subbing layer and an additional reagent layer having at least two distinct zones. In this element buffer is incorporated into the spreading layer by means of either coating on the complete element or ball milling buffer into the spreading layer prior to coating.

In all embodiments the layers are generally in fluid contact with each other, meaning that fluids (reagents for example buffer) can be transported between superposed regions of adjacent zones. In other words, when the element is contacted with an aqueous fluid, all reagents of the analytical composition of this invention are mixed sequentially as stated hereinbefore.

Useful spreading layers can be prepared using fibrous materials, either mixed with a suitable binder material or woven into a fabric, as described in U.S. Pat. No. 4,292,272 (issued Sep. 29, 1981 to Kitajima et al), polymeric compositions or particulate materials, for example a blush polymer such as disclosed in U.S. Pat. No. 3,992,158, beads bound together with or without binding adhesives, as described in U.S. Pat. Nos. 4,258,001 (issued Mar. 24, 1981 to Pierce et al) and 4,430,436 (issued Feb. 7, 1984 to Koyama et al) and Japanese Patent Publication 57(1982)-101760. Particularly useful spreading layers comprise barium sulphate or titanium dioxide. Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The elements of this invention can also contain one or more other addenda commonly put in the elements for various manufacturing or operational advantages. Such addenda include surfactants, bacteriostats, buffers, solvents, hardeners and other materials known in the art.

The layers can be coated on transparent supports such as polyethylene terephthalate. Other supports are well known in the art.

Besides the references noted above, suitable element components are described also, for example, in U.S. Pat. Nos. 4,042,335 (issued Aug. 16, 1977 to Clement), 4,132,528 (issued Jan. 2, 1979 to Eikenberry et al), and 4,144,306 (issued Mar. 13, 1979 to Figueras).

EXAMPLES OF THE INVENTION

Dye 2 of Table 2 was tested in the following dry analytical element. The element was prepared according to procedures known in the dry analytical art as described in the aforementioned patents.

| LITHIUM ELEMENT | | |
|---|---|---|
| | Coverage g/m2 | |
| | Useful Range | Actual Range |
| Reagent/Spreading Layer | | |
| Barium Sulfate | 75–120 | 100 |
| Cellulose Acetate | 1–20 | 8 |
| Surfactant TX-100 | 0.2–2 | 0.7 |
| Estane | 1–5 | 3 |
| o-Xylene | 59–68 | 65 |
| Subbing Zone (pH 11) | | |
| Polyvinylpyrollidone | 2–12 | 4 |
| Buffer | 2–10 | 4 |
| Reagent Layer Zone 1 (pH 7.0) | | |
| Hardened Gelatin | 4–24 | 10 |
| Surfactant F-35 | 0.005–0.1 | 0.01 |
| Reagent Layer Zone 2 (pH 7.0) | | |
| Unhardened Gelatin | 4–24 | 12 |
| Surfactant F-35** | 0.005–0.1 | 0.01 |
| 14-crown-4-ether Dye | 0.2–1.0 | 0.6 |
| 2,4-Di-n-amylphenol* | 2–10 | 3.2 |

Buffers: The buffer used is specified in tables 3 and 4. CAPS pH 11, 4-aminobutyric acid pH 11, Phosphate pH 11.7 arginine pH 12.3 can be substituted.
*Other Organic Solvents such as 2,4-di-tert-amyl phenol; N-n-butylacetanilide or diethyllauramide can be used.
**Other Surfactants such as the Alkanol-XC sodium naphthalene sulfonate mixture from DuPont can be used.

The elements were kept at 25° C. and 15% relative humidity until tested. Then they were spotted with solutions containing human serum spiked with lithium chloride. The serum contained actual lithium concentrations varying between 0.27 and 10.59 mM. After 5 minutes incubation at 37° C., the reflectance densitometer at λ=600 nm. The lithium concentrations obtained from these reflections densities are the predicted concentrations for the various spiked lithium levels. The results for each dye tested is presented in Tables 3 and 4.

TABLE 3

| ASSAY WITH DYE 2 OF TABLE 1 | | |
|---|---|---|
| $D_R$ | ACTUAL | PREDICTED |
| 0.68915 | 0.28 | 0.22 |
| 0.69625 | 0.50 | 0.37 |
| 0.71936 | 0.80 | 0.88 |
| 0.72882 | 1.00 | 1.11 |
| 0.75111 | 1.52 | 1.68 |
| 0.78255 | 2.50 | 2.57 |
| 0.81521 | 3.72 | 3.59 |
| 0.85550 | 5.00 | 5.00 |
| 0.98290 | 10.60 | 10.50 |

Buffer; CAPS is pH 11, 2.0 g/m²

TABLE 4

| ASSAY USING DYE 2 OF TABLE 1 | | |
|---|---|---|
| $D_4$ | ACTUAL | PREDICTED |
| 0.81035 | 0.28 | — |
| 0.82587 | 0.50 | 0.49 |
| 0.83864 | 0.80 | 0.89 |

TABLE 4-continued

| ASSAY USING DYE 2 OF TABLE 1 | | |
|---|---|---|
| D$_4$ | ACTUAL | PREDICTED |
| 0.85304 | 1.00 | 1.36 |
| 0.86021 | 1.52 | 1.59 |
| 0.88924 | 2.50 | 2.58 |
| 0.91160 | 3.72 | 3.39 |
| 0.95331 | 5.00 | 4.97 |
| 1.08228 | 10.60 | 10.62 |

Buffer; 4-Aminobutyric Acid pH 11, 4.0 g/m$^2$
Buffer; 4-Aminobutyric Acid pH 11, 2.0 g/m$^2$ Comparison of the actual values to the predicted values in Tables 3 and 4 shows that the dyes selected for use in the analytical elements of the invention provide quantitative analysis of lithium ion in serum containing interferants such as sodium, potassium, calcium, magnesium, iron and proteins. Dye 2 was tested in a similar element and gave similar results. Moreover it is expected that each of the dyes of table 1 having a delta absorbance of at least 0.12 will provide similar results.

The invention has been described in detail with particular reference to preferred embodiments thereof, but it will be understood that variations an modifications can be effected within the spirit and scope of the invention.

We claim:

1. A multilayer dry analytical element for quantitatively assaying lithium comprising a spreading layer, and a reagent layer wherein sufficent buffer is present above the reagent layer to establish a pH of at least 9 and the reagent layer comprises a 14-Crown-4-ether derivative according to structure I.

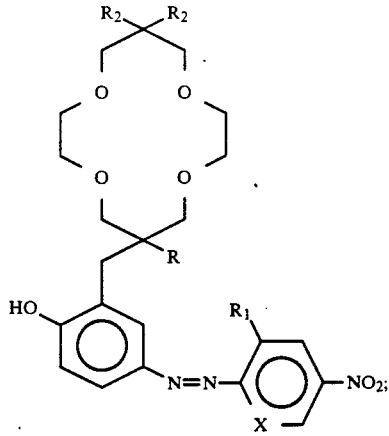

wherein said derivative is selected from the group consisting of dye numbers 1-7 according to table 1

TABLE 1

| Dye No. | R | R$_1$ | R$_2$ | X |
|---|---|---|---|---|
| 1 | n-C$_{12}$H$_{25}$ | SO$_2$CH$_3$ | CH$_3$ | CH |
| 2 | n-C$_{12}$H$_{25}$ | NO$_2$ | CH$_3$ | CH |
| 3 | CH$_3$ | SO$_2$N(n-C$_6$H$_{13}$)$_2$ | CH$_3$ | CH |
| 4 | CH$_2$C$_6$H$_5$ | SO$_2$N(n-C$_6$H$_{13}$)$_2$ | CH$_3$ | CH |
| 5 | CH$_2$C$_6$H$_5$ | SO$_2$N(CH$_3$)-n-C$_{18}$H$_{37}$ | CH$_3$ | CH |
| 6 | CH$_3$ | NO$_2$ | n-C$_7$H$_{15}$ | CH |
| 7 | n-C$_{12}$H$_{25}$ | H | CH$_3$ | N |

2. The element of claim 1 wherein the reagent layer has two distinct zones.

3. The element of claim 1 or 2 wherein the buffer is incorporated in a subbing layer between the spreading layer and the reagent layer.

4. The element of claim 1 or 2 wherein the buffer is incorporated in the spreading layer.

5. The element of claim 1 or 2 wherein dye 1 or 2 of table 1 is used in the element.

6. The element of claim 1 or 2 wherein the buffer is present in amount sufficient to establish a pH of at least 10.

* * * * *